United States Patent [19]

Sundermann et al.

[11] 4,049,630

[45] Sept. 20, 1977

[54] PROCESS FOR PREPARATION OF S-TRIAZINE PREPOLYMERS

[75] Inventors: Rudolf Sundermann, Leverkusen; Rolf Pütter, Duesseldorf; Ernst Grigat, Odenthal, all of Germany

[73] Assignee: Bayer Aktiengesellschaft, Leverkusen, Germany

[21] Appl. No.: 631,560

[22] Filed: Nov. 13, 1975

[30] Foreign Application Priority Data

Dec. 3, 1974   Germany ............................ 2457081

[51] Int. Cl.² .............................................. C08G 73/06
[52] U.S. Cl. .............................. 260/47 R; 260/47 CZ; 260/47 CP; 260/49; 260/50; 260/77.5 R
[58] Field of Search ................... 260/47 R, 47 CP, 49, 260/47 CZ, 77.5 R, 50

[56] References Cited

U.S. PATENT DOCUMENTS

| 2,481,156 | 9/1949 | Schaefer | 260/2 |
| 3,108,029 | 10/1963 | Wohnsiedler et al. | 156/330 |
| 3,654,192 | 4/1972 | Vogel | 260/2 R |
| 3,960,783 | 6/1976 | Seltzer et al. | 260/2 R |

Primary Examiner—Lester L. Lee
Attorney, Agent, or Firm—Burgess, Dinklage & Sprung

[57] ABSTRACT

Process for the preparation of s-triazine prepolymers which comprises
a. condensing a hydroxy compound which has 2 or more alcoholic hydroxyl groups;
b. condensing the resulting condensation product with an aromatic hydroxy compound; and
c. thereafter reacting the free hydroxyl groups of the condensation product obtained from (b) with cyanogen halide and in the presence of a base.

21 Claims, No Drawings

PROCESS FOR PREPARATION OF S-TRIAZINE PREPOLYMERS

BACKGROUND

This invention relates to new s-triazine prepolymers and a process for their preparation.

It is known to polymerise difunctional or polyfunctional aromatic cyanic acid esters to give high molecular polytriazines (German Published Specification 1,190,184). The polymerisation takes place strongly exothermically and with relatively great shrinkage, via a so-called "B-stage" (Kunststoffe, volume 58, page 829 (1968)); this results in various disadvantages, particularly as regards conversion to, for example, glass fibre-reinforced mouldings and, for example, the dimensional accuracy of the mouldings produced. It has already been proposed to avoid the disadvantages of the direct polymerisation by preparing prepolymers by interrupting the polymerisation, by cooling, when about 30 to 65% of the cyanic acid ester groups have reacted (British Patent No. 1,305,762).

SUMMARY

It has now been found that new s-triazine prepolymers are obtained when a. aliphatic, cycloaliphatic or aromatic dihydroxy or polyhydroxy compounds are condensed with more than $\frac{1}{2}$ mol of cyanuric chloride per hydroxyl group and b. the resulting condensation product is condensed with an aromatic dihydroxy or polyhydroxy compound in such a way that more than 1 hydroxyl group equivalent of the aromatic dihydroxy or polyhydroxy compound is used per unconverted chloride atom of the condensation product obtained, and c. thereafter, the free hydroxyl groups of the condensation product thus obtained are reacted with a cyanogen halide in the presence of a base.

DESCRIPTION

The starting compound, cyanuric chloride, is known.

The aliphatic, cycloaliphatic and aromatic dihydroxy and polyhydroxy compounds which can be used in the process according to the invention correspond to the general formula

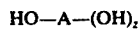    (I)

in which
  A denotes an aliphatic, cycloaliphatic or aromatic radical and
  z denotes an integer which is smaller by at least the number 1 than the number of carbon atoms of the radical A which are capable of substitution.

Aliphatic, cycloaliphatic and aromatic dihydroxy or polyhydroxy compounds which can be used as starting compounds for the process according to the invention are known in large numbers. For practical purposes, all aliphatic, cycloaliphatic and aromatic and aromatic-heterocyclic compounds which have 2 or more alcoholic hydroxyl groups and are optionally substituted further can be used, provided the possible substituents are stable and do not themselves react under the conditions of the process according to the invention.

In particular, the aromatic hydroxy compounds which can be used in the process according to the invention correspond to the general formula

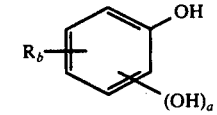    (II)

in which
  R denotes hydrogen, haloen, alkyl or phenyl, and it is not necessary for several radicals R to be identical, or two radicals R which are substituents on adjacent C atoms can also form, conjointly with these, a carbocyclic or heterocyclic 5-membered or 6-membered ring,
  $a$ represents one of the numbers 1, 2 or 3 and $b$ represents $5 - a$.

At the same time, $a$ preferably represents one of the numbers 1 or 2, and especially the number 1.

Of the radicals R, preferably 1 or 2 and especially one, have a different meaning than hydrogen, whilst the remainder represent hydrogen.

A further group of the aromatic dihydroxy and polyhydroxy compounds which can be used in the process according to the invention in particular correspond to the formula

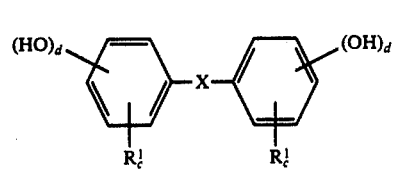    (III)

in which
  X represents oxygen, the sulfonyl group ($SO_2$), the carbonyl group (CO), a $CH_2$ chain, with up to 6, preferably up to 3, C atoms, which is optionally substituted by lower alkyl radicals, preferably methyl, or phenyl, a cycloaliphatic or aromatic 5-membered or 6-membered ring or a single bond and
  $R^1$ has the meaning indicated above for R or represents the grouping

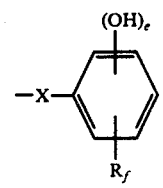

in which
  X and R have the abovementioned meaning,
  $e$ represents one of the numbers 1, 2 or 3,
  $f$ represents $5 - e$ and
  $c$ represents $5 - d$ and
  $d$ denotes one of the numbers 1, 2 or 3.

$d$ and $e$ preferably represent the numbers 1 or 2, especially the number 1.

Of the $c$ radicals $R^1$ and the $f$ radicals R, in each case preferably one or 2, especially one, radical has a different meaning than hydrogen whilst the remainder represent hydrogen.

Amongst the halogens (fluorine, chlorine, bromine and iodine), fluorine, chlorine and bromine may be mentioned preferentially.

Alkyl radicals which may be mentioned are straight-chain and branched alkyl radicals with up to 9, preferably with up to 5, C atoms, for example methyl, ethyl, propyl, isopropy, n-butyl, isobutyl, t-butyl and the isomeric pentyl radicals, especially methyl and ethyl and tert.-butyl.

The following may be mentioned as examples of compounds corresponding to the general formula II: o-, m- and p-dihydroxybenzene, 2-tert.-butylhydroquinone, 2,4-dimethylresorcinol, 2,5-di-tert.-butylhydroquinone, tetramethylhydroquinone, 2,4,6-trimethylresorcinol, 2,6-di-tert.-butylhydroquinone, 4-chlororesorcinol, 4-tert.-butylpyrocatechol, and dihydroxynaphthalenes such as, for example, 1,4-, 1,5-, 1,6-, 1,7-, 2,6- and 2,7-dihydroxynaphthalene.

The following may be mentioned as examples of compounds corresponding to the general formula III: dihydroxydiphenyls such as, for example, 4,4'-dihydroxydiphenyl, 2,2'-dihydroxydiphenyl, 3,3', 5,5'-tetramethyl-4,4'-dihydroxydiphenyl 3,3', 5,5'-tetrachloro-4,4'dihydroxydiphenyl, 3,3',5,5'-tetrachloro-2,2'-dihydroxydiphenyl, 2,2',6,6'-tetrachloro-4,4'-dihydroxydiphenyl, 4,4'-bis-[(3-hydroxy) phenoxy]-diphenyl and 4,4'-bis-[(4-hydroxy)phenoxy]-diphenyl; 2,2'-dihydroxy-1,1'-binaphthyl; dihydroxydiphenyl ethers, such as, for example, 4,4'-dihydroxydiphenyl ether, 3,3', 5,5'-tetramethyl-4,4'-dihydroxydiphenyl ether, 3,3', 5,5'-tetrachloro-4,4'-dihydroxydiphenyl ether, 4,4'-bis-[p-hydroxyphenoxy]-diphenyl ether, 4,4'-bis-[p-hydroxyphenylisopropyl]-diphenyl ether, 4,4'-bis-[p-hydroxyphenoxy]-benzene, 4,4'-bis-[m-hydroxyphenoxy]-diphenyl ether and 4,4'-bis-[4(4-hydroxyphenoxy)- phenylsulphonyl]-diphenyl ether, diphenylsulphones, such as, for example, 4,4'-dihydroxydiphenylsulphone, 3,3', 5,5'-tetramethyl-4,4'-dihydroxydiphenylsulphone, 3,3', 5,5'-tetrachloro-4,4'-dihydroxydiphenylsulphone, 4,4'-bis-[p-hydroxyphenylisopropyl]-diphenylsulphone, 4,4'-bis-[(4-hydroxy)-phenoxy]-diphenylsulphone, 4,4'-bis-[(3-hydroxy)-phenoxy]-diphenylsulphone, 4,4'-bis-[4-(44-hydroxyphenylisopropyl)- phenoxy]-diphenylsulphone, 4,4'-bis-[4-(4-hydroxyphenyl-sulphonyl)-phenoxy]-diphenylsulphone and 4,4'-bis-[4-(4-hydroxy)-diphenoxy]-diphenylsulphone, dihydroxydiphenylalkanes, such as, for example, 4,4'-dihydroxydiphenylmethane, 4,4'-bis-[p-hydroxyphenyl]-diphenylmethane 2,2-bis-(p-hydroxyphenyl)-propane, 2,2-bis:(3,5-dimethyl-4-hydroxyphenyl)-propane, 2,.2-bis-(3,5-dichloro-4-hydroxyphenyl)-propane, 1,1-bis-[p-hydroxyphenyl]-cyclohexane, bis-[2-hydroxy-1-napthyl]-methane and 1,2-bis-[p-hydroxyphenyl]-1,1,2,2-tetramethylethane, 4,4'-dihydroxybenzophenone, 4,4 α-bis-(4-hydroxy)-phenoxybenzophenone, 1,4-bis[p-hydroxyphenylisopropyl]-benzene, phloroglucinol, pyrogallol and 2,2', 5,5'-tetrahydroxydiphenylsulphone.

In particular, the aliphatic and cycloaliphatic hydroxy compounds which can be used in the process according to the invention correspond to the general formula $$HO-A^1-(OH)_u \quad (IV)$$

in which

A[1] denotes an optionally substituted aliphatic or cycloaliphatic radical and u represents z, preferably one of the numbers 1 to 5, especially 1, 2 or 3.

Aliphatic radicals which may be mentioned are straightchain and branched aliphatic radicals with 2 to 36, preferably 2 to 20, and especially 2 to 18, carbon atoms.

Cycloaliphatic radicals which may be mentioned are those with up to 36, preferably 5 to 18, carbon atoms, especially cyclopentane and cyclohexane.

Of course, both the aliphatic and the cycloalphatic radicals can be substituted by such substituents as are stable, and do not themselves react, under the conditions of the process according to the invention. Examples of these which may be mentioned are ester, ether or urethane radicals. Furthermore, the aliphatic radicals can also contain double and/or triple bonds, that is to say they can be alkenyl or alkinyl radicals.

A further particular group of possible aliphatic and cycloaliphatic dihydroxy and polyhydroxy compounds are those of the formula

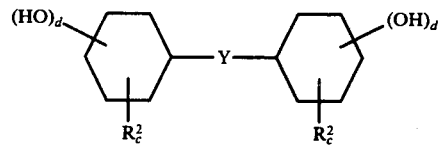

(V)

in which

Y represents oxygen, the sulphonyl group (SO₂) the carbonyl group (CO), a CH₂ chain with up to 6, preferably with up to 3, C atoms which is optionally substituted by lower alkyl radicals, preferably methyl, or phenyl, a cycloalphatic or aromatic 5-membered or 6-membered ring or a simple bond and R² has the meaning indicated above for R or represents the grouping

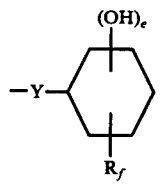

in which

Y, R, e and f have the abovementioned meaning, and c and d have the abovementioned meaning.

The following may be mentioned as examples of compounds corresponding to the general formula IV: glycol; 1,2-propanediol; 1,3-propanediol; 3-chloro-1,2-propanediol; 1,2-butanediol; 1,4-butanediol; 2,3-butanediol; 2-methyl-1,3-propanediol; 1,5-pentanediol; 2,2-dimethyl-1,3-propanediol; 1,6-hexanediol; 2,5-hexanediol; 2-methyl-2,4pentanediol; 3-methyl-2,4-pentanediol; 2,3-dimethyl-2,3-butanediol; 2-methyl-2-propyl-1,3-propanediol; 2,2-diethyl-1,3-propanediol; octanediols, for example 1,8-octanediol; 2,5-dimethyl-2,5-hexanediol; 2,4,4-trimethyl-1,3-pentanediol; 1,12-octane-decanediol; 2-butene-1,4-diol; 2-methylene-1,3-propanediol; 2-butine-1,4-diol; glycerol and trimethylolpropane; 2-methyl-2-hydroxymethyl-1,3-propanediol; 1,2,6-hexanetriol; 2-ethyl-2-hydroxymethyl-1,3-propanediol; pentaerythritol; quinitol; mannitol; sorbitol; 1,2-cyclohexanediol; 1,4-cyclohexanediol; 2,4-dihydroxy-1,1,3,3-tetramethyl-cyclobutane; 1,4-bis-hydroxymethyl-cyclohexane; 2,2-bis-(4-hydroxy-cyclohexyl)-propane; 2-methyl-2,4-bis-(4-hydroxy-cyclohexyl)-pentane; diethylene glycol; triethylene glycol; tetraethylene glycol; octaethylene glycol; polyethylene glycol;

dipropylene glycols; tripropylene glycols; polyoxymethylene; polypropylene glycol.

It is also possible to use polyesters with hydroxyl groups which are still free, for example reaction products of polyhydric, preferably dihydric, and optionally additionally trihydric, alcohols with polybasic, preferably dibasic, carboxylic acids. In place of the free polycarboxylic acids it is also possible to use the corresponding polycarboxylic acid anhydrides or corresponding polycarboxylic acid esters of lower alcohols or their mixtures for the preparation of the polyesters. The polycarboxylic acids can be of aliphatic, cycloaliphatic, aromatic and/or heterocyclic nature and can optionally be substituted, for example by halogen atoms, and/or unsaturated. As examples thereof there may be mentioned succinic acid, adipic acid, suberic acid, azelaic acid, sebacic acid, phthalic acid, isophthalic acid, trimellitic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimeric and trimeric fatty acids such as oleic acid, optionally mixed with monomeric fatty acids, terephthalic acid dimethyl ester and terephthalic acid bis-glycol ester. Examples of possible polyhydric alcohols are ethylene glycol, 1,2-propylene glycol and 1,3-propylene glycol, 1,4-butylene glycol and 2,3-butylene glycol, 1,6-hexanediol, 1,8-octanediol, neopentyl glycol, cyclohexanedimethanol (1,4-bishydroxymethylcyclohexane), 2-methyl-1,3-propanediol, glycerol, trimethylolpropane, 1,2,6-hexanetriol, 1,2,4-butanetriol, trimethylolethane, pentaerythritol, quinitol, mannitol and sorbitol, methylglycoside and also diethylene glycol, triethylene glycol, tetraethylene glycol, polyethylene glycols, dipropylene glycol, polypropylene glycols, dibutylene glycol and polybutylene glycols. The polyesters can in part have terminal carboxyl groups. Polyesters obtained from lactones, for example ε-caprolactone, or from hydroxycarboxylic acid, for example ω-hydroxycaproic acid, can also be employed.

Polyethers which still have free hydroxyl groups, preferably those having two to three hydroxyl groups, can also be used; these polyethers are of a type which are in themselves known and are prepared, for example, by polymerisation of epoxides such as ethylene oxide, propylene oxide, butylene oxide or epichlorohydrin with itself, for example in the presence of $BF_3$, or by addition reaction of these epoxides, optionally as a mixture or successively, with starting components having reactive hydrogen atoms, such as alcohols or amines, for example water, ethylene glycol, 1,3-propylene glycol or 1,2-propylene glycol or trimethylolpropane.

Polyhydroxy compounds which already contain urethane groups can also be used if they contain at least two, preferably two or three, free hydroxyl groups.

Representatives of these compounds to be used according to the invention are described, for example, in High Polymers, volume XVI, "Polyurethanes, Chemistry and Technology", edited by Saunders-Frisch, Interscience Publishers, New York, London, volume I, 1962, pages 32–42 and pages 44–54 and volume II, 1964, pages 5–6 and 198–199, and also in the Kunststoff-Handbuch (Plastics Handbook), volume VII, Vieweg-Hochtlen, Carl-Hanser-Verlag, Munich, 1966, for example on pages 45 to 71.

The reaction of the aliphatic, cycloaliphatic and aromatic dihydroxy or polyhydroxy compounds with cyanuric chloride in process step (a) can, like the further reaction (condensation) of the reaction product obtained in process step (a) with the aromatic dihydroxy or polyhydroxy compound in the subsequent process step (b), be carried out in the melt at 100° to 250° C, preferably at 150° to 220° C, especially at between 170° and 200° C; the hydrogen chloride produced at the same time escapes as a gas from the melt at these temperatures. Of course it is also possible to work under reduced pressure, preferably down to about 0.01 bar, especially between 0.2 and about 0.8 bar, in order to remove the hydrogen chloride. However, the reaction can also be carried out in solution and/or suspension in the presence of about 1 mol of base per mol of the hydrogen chloride to be split off, at temperatures of about 0° to about 150° C, preferably 0° to about 100° C, especially in the range between 20° and 70° C.

Solvents which can be used for the condensation in solution and/or suspension are, for example, water and lower aliphatic alcohols such as methanol, ethanol, propanol and isopropanol; aliphatic ketones such as acetone, methyl ethyl ketone, diethyl ketone, methyl isopropyl ketone and methyl isobutyl ketone; aliphatic or aromatic hydrocarbons, the aliphatic hydrocarbons used being preferably the fractions which arise on distillation of the naturally occurring mixtures, such as petroleum ether, light gasoline or gasoline, whilst exampls of aromatic hydrocarbons which may be mentioned are benzene, toluene and the xylenes; aliphatic and aromatic chlorohydrocarbons, such ad dichloromethane, dichloroethane, perchloroethylene, chlorobenzene and dichlorobenzene; ethers such as diethyl ether and diisopropyl ether; nitrohydrocarbons such as nitromethane, nitrobenzene and nitrotoluene, and amides, such as dimethylformamide, dimethylacetamide and N-methylpyrrolidone.

Examples of bases which can be used for the condensation in solution and/or suspension are alkali metal hydroxides such as sodium hydroxide and potassium hydroxide; alkali metal carbonates such as sodium carbonate and potassium carbonate; alcoholates such as sodium methylate and potassium tert.-butylate, and also tertiary amines such as triethylamine, diethylaniline and pyridine.

In general, the reaction of the aliphatic, cycloaliphatic and aromatic dihydroxy or polyhydroxy compounds with cyanuric chloride, according to (a), is carried out by bringing the chosen amounts of the reactants together and heating the mixture to the chosen reaction temperature. The reaction has ended when the evolution of hydrogen chloride ceases. It is also possible to ascertain, by measuring the hydrogen chloride evolved, whether the theoretically calculated amount has been split off and the reaction has accordingly been completed. In the case of the melt condensation, further working up and purification of the condensation product is in general not required.

The condensation according to (a) can also be carried out in solution and/or suspension. For this purpose, cyanuric chloride is dissolved and/or suspended in the chosen solvent and the appropriate amounts of dihydroxy or polyhydroxy compound and base are fed in. The sequence of addition of the two latter reactants is optional.

The course of the reaction, and the end of the reaction can be followed and recognised in accordance with known analytical methods from the increase in the chloride ion concentration. After completion of the reaction, the reaction mixture can be worked up in accordance with customary methods; suitably, the hydrochloride of the base used, formed as a by-product, is first separated off or dissolved in water, after which the aqueous solution is separated off. It is then possible to remove the solvent, for example by distillation, and to isolate the condensation product, hereinafter referred to as condensate (a).

The subsequent reaction of the resulting condensate (a) with an aromatic dihydroxy or polyhydroxy compound can be carried out in the same manner as the preparation of the condensate (a).

For example, the reaction of the condensate (a) with the aromatic dihydroxy or polyhydroxy compound can be carried out in the melt at 100° to 250° C, preferably at 150° to 220° C, especially at between 170° and 200° C. In doing so, the hydrogen chloride formed at the same time escapes as a gas from the melt. Of course, it is also possible to work under reduced pressure, as described above, in order to remove the hydrogen chloride. Equally, it is however also posible to carry out process step (b) in solution and/or suspension in the presence of about 1 mol of base per mol of hydrogen chloride to be split off, at temperatures of about 0° to about 150° C, preferably 0° to about 100° C, especially in the range between 20° and 70° C.

In the condensation according to (b) in solution and/or suspension it is possible to use, as solvents, the same solvents as those mentioned above for the reaction according to (a).

At bases it is again possible to use, in the condensation according to (b) in solution and/or suspension, the base mentioned above for the reaction according to (a).

As in the case of the condensation according to (a), the condensation according to (b) can also be carried out by bringing together the chosen amounts of the reactants and heating the mixture to the chosen reaction temperature. The reaction is complete when the evolution of hydrogen chloride ceases. In the case of the melt condensation, further working up and purification of the condensation product is in general not necessary.

The condensation according to (b) can also be carried out in solution and/or suspension. For this purpose, the condensation product (a) is dissolved and/or suspended in the chosen solvent and reacted with the corresponding amount of dihydroxy or polyhydroxy compound and base. The sequence of addition of the individual reactants is optional.

The course and the end of the reaction can be followed and recognised in accordance with known analytical methods from the increase in the chloride ion concentration. After completion of the reaction, the reaction mixture can be worked up in accordance with customary methods; suitably, the hydrochloride of the base used, formed as a by-product, is first separated off or dissolved in water, after which the aqueous solution is separated off. The sovent can then be removed by distillation and the condensation product, hereafter referred to as a condensate (b), can be isolated.

The subsequent reaction of the condensate (b) with cyanogen halides can be carried out in accordance with known methods. For example, the condensate (b) and the cyanogen halides can first be suspended and/or dissolved in a solvent and the base, optionally in solution, can be added. It is, however, also possible first to take the condensate (b) and to add the cyanogen halide and the base, both optionally in solution, or first to take the cyanogen halide and add the condensate and the base, both optionally in solution.

As solvents it is possible to use the solvents as have been mentioned for the first stage (a) of the process according to the invention; equally, the solvents known for the reaction of phenolic hydroxyl groups with cyanogen halide can be used. The reaction can also be carried out in aqueous suspension and/or using mixtures or emulsions of the abovementioned solvents with water in solution, suspension or emulsion.

Bases which can be used in this reaction stage (c) are the bases mentioned for condensation stages (a) and (b) as well as the bases customary for the reaction of phenolic hydroxyl groups wity cyanogen halide.

The cyanogen halide which can be used is in particular the industrially easily accessible cyanogen chloride or cyanogen bromide. In general, a molar ratio of phenolic hydroxyl groups to cyanogen halide to base of 1:1:1 is observed. However, a slight excess of cyanogen halide can be of advantage. The reaction can be carried out in the temperature of $-40°$ to $+65°$ C, preferably between 0 and 65° C, and especially between 0° and 30° C. Preferably, the reaction, when using cyanogen chloride, would be carried out below the boiling point of the latter (13° C), whilst when using cyanogen bromide temperatures in the upper part of the temperature range mentioned, for example temperature of above 50° C, can also be used.

After completion of the reaction, the hydrochloric acid salt formed is separated off in accordance with known methods, the methods depending on the solvent used. In purely organic solution, the chloride formed in general precipitates entirely or partially and can be separated off mechanically in accordance with known methods. However, when using water-immiscible solvents, the chloride can also be dissolved by means of water and separated off as an aqueous solution. When using aqueous organic emulsions the chloride can be at least partially dissolved in the aqueous phase and can be dissolved completely by adding further water and be separated off with the aqueous phase after breaking the emulsion. After removing the solvent in the usual manner, the s-triazine prepolymer is obtained in good yield.

It can also be advantageous to carry out both condensation stages and the subsequent reaction with cyanogen halide in a so-called one-pot process. In that case it can be advantageous, if the condensation is carried out in the presence of a solvent, to use the same solvent and, where appropriate, the same base, for all process stages.

The process according to the invention can be illustrated by the following reaction schemes:

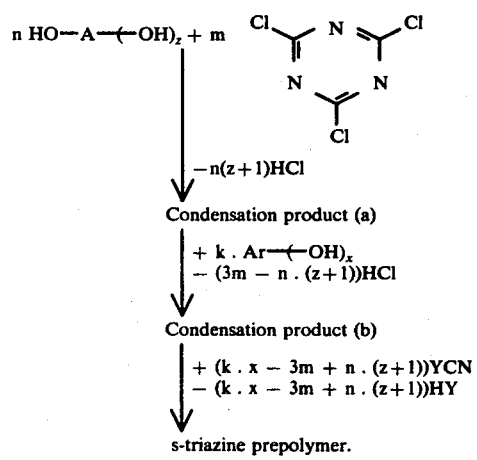

Herein
A has the abovementioned meaning,
Ar represents an aromatic radical,
Y denotes halogen,
z denotes an integer which is less by at least the number 1 than the number of carbon atoms of the radical A which are capable of substitution,
x represents one of the numbers from 2 to 5 and $n$, $m$ and $k$ denote integers which fulfill the conditions that $n \cdot z$ is less than $3m$ and $k \cdot x$ is greater than $3m - n \cdot (z+1)$.

The number of cyanate groups still present in the s-triazine prepolymer is found to be $k \cdot x - 3m + n(z+1)$, from the numerical values of $k$, $m$, $n$, $x$ and $z$, which also determine the degree of crosslinking of the s-triazine prepolymer.

The process according to the invention can further be illustrated with the aid of the following equation, given by way of example, in which the formulae of the condensates (a) and (b) and of the s-triazine prepolymer are reproduced in an idealised form.

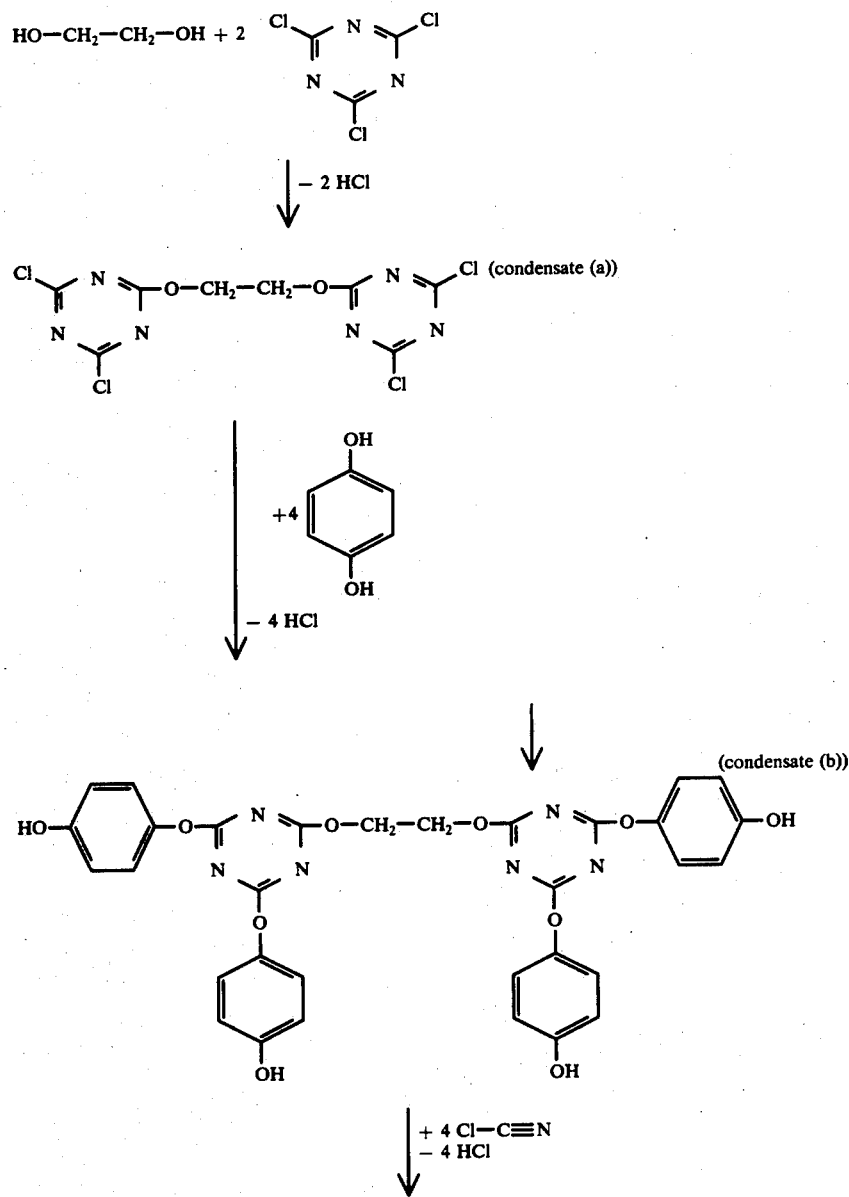

-continued

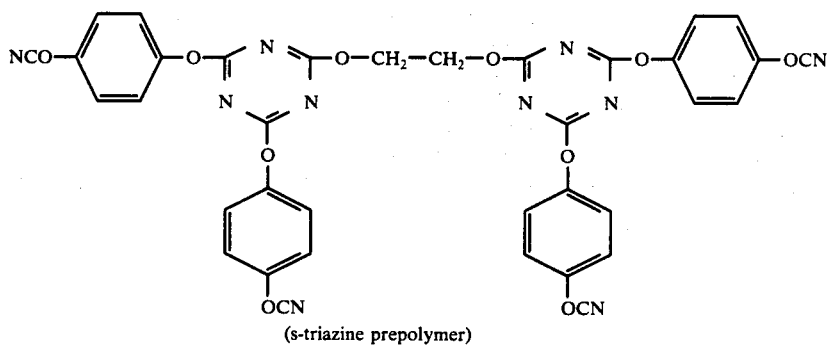
(s-triazine prepolymer)

The new s-triazines of the prepolymers obtainable in accordance with the process of the invention cannot be characterised by a general formula, because of the diverse possibilities in choosing the ratio of the starting compounds and of the diverse possibilities, resulting from the three functional groups of the cyanuric chloride and the two or more functional groups of the dihydroxy and polyhydroxy compounds, of condensation of the starting compounds, which furthermore will not lead to a single reaction product but to many of the conceivable condensation products, in statistical distribution in a mixture; rather, the prepolymers are unambiguously defined by their process of preparation.

As compounds, the new s-triazine prepolymers are thus characterised in that they are obtained when (a) aliphatic, cycloaliphatic or aromatic dihydroxy or polyhydroxy compounds are condensed with more than 1/3 mol of cyanuric chloride per hydroxyl group and (b) the resulting condensation product is condensed with an aromatic dihydroxy or polyhydroxy compound in such a way that more than 1 hydroxyl group equivalent of the aromatic dihydroxy or polyhydroxy compound is used per unreacted chlorine atom of the condensation product obtained, and (c) thereafter the free hydroxyl groups of the condensation product thus obtained are reacted with a cyanogen halide in the presence of a base.

The new s-triazine prepolymers according to the invention, and the process for their preparation, have various advantages. The new s-triazine prepolymers are of waxy consistency and are easily processable. They do not contain any monomeric cyanic acid esters; this is an advantage for the polymerisation carried out at elevated temperatures, since monomeric cyanic acid esters in some cases have extremely unpleasant properties (for example odour, or irritation of the mucous membranes). As already mentioned, little or no shrinkage occurs on polymerisation of the s-triazine prepolymers, in contrast to the polymerisation of the cyanic acid esters, so that mouldings of substantially greater dimensional accuracy are obtainable.

The new s-triazine prepolymers which can be obtained in accordance with the process of the invention are valuable oligomers. They can be polymerised in accordance with known processes, such as the process of German Printed Application 1,190,184, to give high-molecular polytriazines which can find application in various fields, for example as fibre-reinforced plastics, pressing or casting resins, adhesives, coating agents or lacquers.

In the examples which follow, the s-triazine prepolymer obtained is described, for brevity, as "prepolymer".

EXAMPLE 1 a. 12.4 g (0.2 mol) of ethylene glycol and 73.8 g (0.4 mol) of cyanuric chloride are dissolved in 300 ml of acetone. 40.4 g (0.4 mol) of triethylamine are added dropwise to this solution over the course of 2 hours at 30°–40° C, whilst stirring. After completion of the reaction, the mixture is stirred for a further 3 hours at 50° C and cooled, and the triethylammonium chloride which has precipitated is filtered off and washed with acetone. The wash acetone is combined with the acetone reaction solution and poured into 2 l of water; the reaction product which hereupon precipitates is subsequently filtered off.

b. 36 g (0.1 mol) of the condensate thus obtained and 91.2 g (0.4 mol) of 2,2-bis-(p-hydroxyphenyl)-propane are dissolved in 400 ml of isopropanol. 40.4 g (0.4 mol) of triethylamine are added dropwise to this solution at 30°–40° C, whilst stirring. The reaction mixture is then boiled for 6 hours under reflux. The triethylammonium chloride which hereupon precipitates is filtered off and the isopropanol is distilled from the reaction mixture. The residue is taken up in 500 ml of methylene chloride and extracted with water, which is discarded. The methylene chloride is distilled from the solution and the residue obtained is the reaction product, in the form of a tough resin.

c. 112 g (0.1 mol) of the condensate thus obtained, together with 40.4 g (0.4 mol) of triethylamine, dissolved in 300 ml of methylene chloride, are added dropwise to a solution of 27 g (0.44 mol) of cyanogen chloride in 200 ml of methylene chloride whilst stirring at 0° C. After completion of the reaction, the triethylammonium chloride which has precipitated is filtered off, the methylene chloride solution is washed with water, which is discarded, and the solvent is then distilled off.

This gives 116 g (95% of theory) of prepolymer having the band typical of the cyanate group in the IR spectrum at 4.5μ.

EXAMPLE 2 a. 11.8 g (0.1 mol) of 1,6-hexanediol and 37 g (0.2 mol) of cyanuric chloride are suspended in 200 ml of methylene chloride. 20.2 g (0.2 mol) of triethylamine dissolved in 50 ml of methylene chloride are added dropwise over the course of 2 hours whilst stirring at 30°–40° C; hereupon, the starting compounds dissolve. After completion of the reaction, the triethylammonium chloride which has precipitated is filtered off and the solvent is then distilled from the filtrate.

b. 41.5 g (0.1 mol) of the condensate thus obtained, 91.2 g (0.4 mol) of 2,2-bis-(p-hydroxyphenyl)-propane in 400 ml of isopropanol, and 40.4 g (0.4 mol) of triethylamine are kept at 30°–40° C, whilst stirring. The mixture is then boiled under reflux for 6 hours. Thereafter the triethylammonium chloride which has precipitated is filtered off, the isopropanol is distilled from the filtrate and the residue is taken up in approximately an equal amount of methylene chloride (400 ml). This solution is washed with water until free from chloride ions. After distilling off the methylene chloride, a tough resin is obtained.

c. 118 g (0.1 mol) of the condensate thus obtained and 40.4 g (0.4 mol) of triethylamine, dissolved in 200 ml of dimethylformamide, are added at 0° C to a solution of 27 g (0.44 mol) of cyanogen chloride in 200 ml of dimethylformamide. The triethylammonium chloride which has precipitated is then filtered off and the solvent is removed by distillation. 120 g (94% of theory) of prepolymer having the characteristic band at 4.5μ in the IR spectrum are obtained.

EXAMPLE 3 a. 15.2 g (0.2 mol) of 1,2-propanediol and 73.8 g (0.4 mol) of cyanuric chloride are dissolved in 300 ml of acetone. 40.4 g (0.4 mol) of triethylamine are added dropwise to this solution over the course of 2 hours at 30°–40° C, whilst stirring. After completion of the reaction, the mixture is stirred for a further 3 hours at 50° C and is cooled, and the triethylammonium chloride which has precipitated is filtered off and washed with acetone. The wash acetone is combined with the reaction solution and poured into 2 l of water, and the reaction product which has precipitated is filtered off.

b. 37 g (0.1 mol) of the condensate thus obtained, 107 g (0.4 mol) of 1,1-bis-(4-hydroxyphenyl)-cyclohexane in 400 ml of isopropanol, and 40.4 g (0.4 mol) of triethylamine are kept at 30°–40° C for 2 hours, whilst stirring, and are then boiled under reflux for 6 hours. Thereafter the triethylammonium chloride which has precipitated is filtered off and the isopropanol is distilled off. The residue is taken up in an equal amount of methylene chloride (400 ml) and this solution is washed with water until free from chloride ions. After distilling the methylene chloride, the reaction product is obtained as a tough resin.

c. 130 g (0.1 mol) of the condensate thus obtained, together with 40.4 g (0.4 mol) of triethylamine, dissolved in 200 ml of dimethylformamide, are added at 0° C to a solution of 27 g (0.44 mol) of cyanogen chloride in 200 ml of dimethylformamide. The triethylammonium chloride which has precipitated is then filtered off and the solvent is removed by distillation. This gives 131 g (95% of theory) of prepolymer having the characteristic band at 4.5μ in the IR spectrum.

EXAMPLE 4 a, 24 g (0.1 mol) of 2,2-bis-(4-hydroxy-cyclohexyl)-propane and 37 g (0.2 mol) of cyanuric chloride are dissolved in 300 ml of acetone. 20.2 g (0.2 mol) of triethylamine are added dropwise over the course of 2 hours, whilst stirring, and the mixture is then stirred for a further 3 hours at 50° C. After cooling, the triethylammonium chloride which has precipitated is filtered off and washed with acetone. The wash acetone is combined with the acetone reaction solution and poured into 2 liters of water; the reaction product which hereupon precipitates is filtered off and dried.

b. 53.6 g (0.1 mol) of the condensate thus obtained and 91.2 g (0.4 mol) of 2,2-bis-(p-hydroxyphenyl)-propane are dissolved in 500 ml of isopropanol. 40.4 g (0.4 mol) of triethylamine are added dropwise to this solution at 30°–40° C, whilst stirring. The reaction mixture is then boiled for 8 hours under reflux. Thereafter, the triethylammonium chloride which has precipitated is filtered off and washed with isopropanol. THe isopropanol solutions are combined and then concentrated. The residue is taken up in 500 ml of methylene chloride and washed with water until free from chloride ions. The methylene chloride is distilled off and the residue obtained is the reaction product in the form of a tough resin.

c. 40.4 g (0.4 mol) of triethylamine are added dropwise over the course of 2 hours to a solution of 27 g (0.44 mol) of cyanogen chloride and 130 g (0.1 mol) of the condensate obtained above in 400 ml of dimethylacetamide at 0° C. The triethylammonium chloride which has precipitated is then filtered off and the solvent is distilled off in vacuo. The residue is taken up in 500 ml of toluene and extracted with water. After distilling the toluene, 128 g (91% of theory) of cyanate resin, with a —OCN band at 4.5μ are obtained.

EXAMPLE 5 a. 18.6 g (0.1 mol) of 4,4'-dihydroxydiphenyl and 37 g (0.2 mol) of cyanuric chloride are dissolved in 200 ml of acetone and 20.2 g (0.2 mol) of triethylamine are added at 30°–40° C. After completion of the reaction, the reaction mixture is stirred for a further 3 hours at 50° C. The triethylammonium chloride which has precipitated is then filtered off and washed with acetone. The acetone phases are combined and added to 2 liters of water. The reaction product where hereupon precipitates is filtered off and dried.

b. 48.2 g (0.1 mol) of the condensate thus obtained and 44 g (0.4 mol) of resorcinol are dissolved in 400 ml of isopropanol. 40.4 g (0.4 mol) of triethylamine are added dropwise to this solution at 30°–40° C, whilst stirring. Thereafter the reaction mixture is boiled for 7 hours under reflux. The triethylammonium chloride which precipitates is the filtered off and washed with isopropanol. The isopropanol solutions are combined and then concentrated. The residue is taken up in 500 ml of methylene chloride and extracted with water. The methylene chloride is distilled off. This gives a residue of the reaction product in the form of a tough resin.

c. 77.6 g (0.1 mol) of the condensate thus obtained and 27 g (0.44 mol) of cyanogen chloride are dissolved in 500 ml of acetone at 0° C. 40.4 g (0.4 mol) of triethylamine are added dropwise over the course of 2 hours at 0° to 10° C, whilst stirring. Thereafter the triethylammonium chloride which has precipitated is filtered off and washed with acetone. The combined acetone phases are concentrated. The residue is taken up in 500 ml of methylene chloride and washed with water until free from chloride ions. After distilling off the methylene chloride, 80 g (91% of theory) of cyanate resin having a —OCN band in the IR spectrum at 4.5μ are obtained.

EXAMPLE 6 a. 28.4 g (0.1 mol) of 2,2-bis-(3,5-dimethyl-4-hydroxyphenyl)-propane and 37 g (0.2 mol) of cyanuric chloride are dissolved in 300 ml of acetone. 20.2 g (0.2 mol) of triethylamine are added dropwise to this solution at 30-40° C and the mixture is then stirred for a further 2 hours at 50° C. The triethylammonium chloride which has precipitated is filtered off and washed with acetone.

The acetone phases are combined and added to 2 liters of water. The product which hereupon precipitates is filtered off and dried.

b. 58.0 g (0.1 mol) of the condensate thus obtained and 44 g (0.4 mol) of hydroquinone are dissolved in 300 ml of isopropanol. 40.4 g (0.4 mol) of triethylamine are added dropwise to this solution at 30°–40° C, whilst stirring. The reaction mixture is then boiled for 8 hours under reflux. The triethylammonium chloride which has precipitated is filtered off and washed with isopropanol. The isopropanol solutions are combined and concentrated. The residue is dissolved in 500 ml of methylene chloride and the solution is washed with water until free from chloride ions. After distilling off the solvent, the reaction product is obtained in the form of a tough resin.

c. 87.4 g (0.1 mol) of the condensate thus obtained and 27 g (0.44 mol) of cyanogen chloride are dissolved in 400 ml of methylene chloride at 0° C. 40.4 g (0.4 mol) of triethylamine are added dropwise over the course of 2 hours at 0° C to 10° C, whilst stirring. After completion of the reaction, the salt which has precipitated is dissolved in 200 ml of water, which is separated off. The organic phase is washed with twice 100 ml of water. Thereafter the solvent is distilled off. This gives 85 g (87% of theory) of cyanate resin with a typical band at 4.5$\mu$ in the IR spectrum.

EXAMPLE 7 a. 36.6 g (0.1 mol) of 2,2-bis-(3,5-dichloro-4-hydroxyphenyl)-propane and 37 g (0.2 mol) of cyanuric chloride are dissolved in 300 ml of acetone. 20.2 g (0.2 mol) of triethylamine are added dropwise to this solution at 30–40° C and thereafter the reaction mixture is stirred for a further 3 hours at 50° C. The triethylammonium chloride which has precipitated is filtered off and washed with acetone. The acetone solutions are combined and added to 2 liters of water. The product which hereupon precipitates is filtered off and dried.

b. 66.2 g (0.1 mol) of the condensate thus obtained and 91.2 g (0.4 of 2,2-bis-(p-hydroxyphenyl)-propane are dissolved in 300 ml of isopropanol. 40.4 g (0.4 mol) of triethylamine are added dropwise to this solution at 30° C –40° C whilst stirring and the reaction mixture is then boiled for 8 hours under reflux. The triethylammonium chloride which has precipitated is filtered off and washed with 100 ml of isopropanol. The isopropanol phases are combined and concentrated. The residue is taken up in 400 ml of methylene chloride and washed with water until free from chloride ions. After stripping off the solvent, the reaction product is obtained as a tough resin.

c. 142.8 g (0.1 mol) of the condensate thus obtained and 27 g (0.44 mol) of cyanogen chloride are dissolved in 500 ml of methalene chloride at 0° C. 40.4 g (0.4 mol) of triethylamine are added dropwise to this solution over the course of 2 hours at 0° C to 10° C. After completion of the reaction, the salt which has precipitated is dissolved in 200 ml of water, which is separated off. The organic phase is washed with twice 100 ml of water. The solvent is then distilled off. 140 g (91.5% of theory) of cyanate resin are obtained. IR spectrum: the -OCN band is at 4.5$\mu$.

EXAMPLE 8 a. 10.6 g (0.1 mol) of diethylene glycol and 37 g (0.2 mol) of cyanuric chloride are dissolved in 150 ml of acetone. 20.2 g (0.2 mol) of triethylamine are added dropwise to this solution at 30°–40° C and the reaction mixture is subsequently stirred for a further 2 hours at 50° C. It is then added to 1.5 liters of water. The product which has precipitated is filtered off, washed and dried.

b. 40.2 g (0.1 mol) of the condensate thus obtained and 91.2 g (0.4 mol) of 2,2-bis-(p-hydroxyphenyl)-propane are dissolved in 300 ml of isopropanol. 40.4 g (0.4 mol) of triethylamine are added dropwise to this solution at 30°–40° C whilst stirring, and the reaction mixture is then boiled for 8 hours under reflux. The triethylammonium chloride which has precipitated is filtered off and washed with 100 ml of isopropanol. The isopropanol phases are combined and concentrated. The residue is taken up in 400 ml of methylene chloride and washed with water until free from chloride ions. After stripping off the solvent, the condensation product is obtained as a tough resin.

c. 116.8 g (0.1 mol) of the condensate thus obtained and 27 g (0.44 mol) of cyanogen chloride are dissolved in 300 ml of methylene chloride at 0° C. 40.4 g (0.4 mol) of triethylamine are added dropwise to this solution over the course of 2 hours at 0° C to 10° C. After completion of the reaction, the salt which has precipitated is dissolved in 200 ml of water, which is separated off. The organic phase is washed with water until free from chloride ions. After stipping off the solvent, 110 g (86.5% of theory) of cyanate resin (IR band at 4.5$\mu$) are obtained.

EXAMPLE 9 a. 19.4 g (0.1 mol) of tetraethylene glycol and 37 g (0.2 mol) of cyanuric chloride are dissolved in 200 ml of acetone. 20.2 g (0.2 mol) of triethylamine are added dropwise to this solution at 30°–40° C, whilst stirring and the reaction mixture is subsequently stirred for a further 3 hours at 50° C. It is then added to 2 liters of water. The product which has precipitated is filtered off and dried.

b. 49.0 g (0.1 mol) of the condensate thus obtained and 91.2 g (0.4 mol) of 2,2-bis-(p-hydroxyphenyl)-propane are dissolved in 400 ml of isopropanol. 40.4 g (0.4 mol) of triethylamine are added dropwise to this solution at 30° C to 40° C, whilst stirring, and the reaction mixture is then boiled for 8 hours under reflux. The triethylammonium chloride which has precipitated is filtered off and washed with 100 ml of isopropanol. The combined isopropanol phases are subsequently concentrated. The residue is taken up in 400 ml of methylene chloride and washed with water until free from chloride ions. After stripping off the solvent, the condensation product is obtained in the form of a tough resin c. 125.6 g (0.1 mol) of the condensate thus obtained and 27 g (0.44 mol) of cyanogen chloride are dissolved in 350 ml of methylene chloride at 0° C. 40.4 g (0.4 mol) of triethylamine are added dropwise to this solution over the course of 2 hours at 0° to 10° C. After completion of the reaction, the triethylammonium chloride which has precipitated is dissolved in 200 ml of water, which is separated off. The organic phase is washed with water until free from chloride ions. After stripping off the solvent, 122 g (90% of theory) of cyanate resin with the typical IR band at 4.5$\mu$ are obtained.

EXAMPLE 10 a. 100 g of a polyester prepared from 1 mol of 1,4-butanediol, 1 mol of ethylene glycol and 2 mols of adipic acid (hydroxyl number 55) and 18.4 g (0.1 mol) of cyanuric chloride are dissolved in 300 ml of acetone. 10.1 g (0.1 mol) of triethylamine are added dropwise to this solution at 30° C to 40° C, whilst stirring, and the reaction mixture is subsequently stirred for a further 3 hours at 50° C. It is then added to 2 liters of water. The product which has precipitated is extracted with 500 ml of methylene chloride. The solvent is distilled off and replaced by 500 ml of isopropanol.

b. 45.6 g (0.2 mol) of 2,2-bis-(p-hydroxyphenyl)-propane are additionally dissolved in the solution of the condensate obtained above. 20.2 g (0.2 mol) of triethylamine are now added to this solution at 30°-40° C whilst stirring and the mixture is then boiled for 8 hours under reflux. The triethylammonium chloride which has precipitated is filtered off and rinsed with 200 ml of isopropanol. The isopropanol phases are combined and concentrated. The residue is taken up in 400 ml of methylene chloride.

c. 13.5 g (0.22 mol) of cyanogen chloride are additionally dissolved at 0° C in the solution of the condensate obtained above. 20.2 g (0.2 mol) of triethylamine are added dropwise to this solution whilst stirring at 0° to 10° C. After completion of the reaction, the salt which has precipitated is dissolved in 200 ml of water, which is separated off. The organic phase is washed with water until free from chloride ions. After distilling off the solvent, 150 g (95% of theory) of cyanate resin are obtained. IR spectrum: —OCN band at 4.5μ, strong ester band at 5.8μ.

What is claimed is:

1. Process for the preparation of s-triazine prepolymers which comprises
    a. condensing a hydroxy compound which has 2 or more alcoholic hydroxyl groups corresponding to the formula HO—A—(OH)$_z$                                                             (I)

in which
        A denotes an aliphatic, cycloaliphatic or aromatic radical and
        z denotes an integer which is smaller by at least the number 1 than the number of carbon atoms of the radical A which are capable of substitution
    with more than 1/3 mol of cyanuric chloride per hydroxyl group at a temperature in the range of 0° to 250° C;
    b. condensing the resulting condensation product with an aromatic hydroxy compound selected from the group consisting of compounds corresponding to the formulae

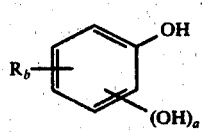
(II)

in which
        R denotes hydrogen, halogen, alkyl or phenyl, and it is not necessary for several radicals R to be identical, or two radicals R which are substituents on adjacent carbon atoms can also form, conjointly with these, a carbocyclic or heterocyclic 5-membered or 6-membered ring,
        a represents one of the numbers 1, 2, or 3 and b represents 5-a and

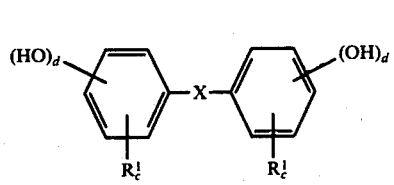
(III)

in which
        X represents oxygen, the sulfonyl group (SO$_2$), the carbonyl group (CO), a CH$_2$ chain with up to 6 carbon atoms which is optionally substituted by lower alkyl radicals, phenyl, a cycloaliphatic or aromatic 5-membered or 6-membered ring or a single bond and
        R$^1$ has the meaning indicated above for R or represents the grouping

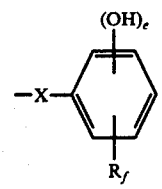

in which
        X and R have the abovementioned meaning,
        e represents one of the numbers 1, 2, or 3,
        f represents 5-e,
        c represents 5-d,
        d denotes one of the numbers 1, 2, or 3 in such a way that more than 1 hydroxyl group equivalent of the aromatic hydroxy compound is used per unconverted chlorine atom of the condensation product obtained from (a) at a temperature in the range of 0° to 250° C; and
    c. thereafter reacting the free hydroxyl groups of the condensation product obtained from (b) with cyanogen halide and in the presence of a base selectd from the group consisting of alkali metal hydroxide, alkali metal carbonate, alcoholate and tertiary amine in amounts which correspond to a molar ratio of phenolic hydroxyl groups to cyanogen halide to base in the range of 1:1:1 to a slight excess of cyanogen halide at a temperature in the range of −40' to +65° C.

2. Process of claim 1 wherein the hydroxy compound used in step (a) has the formula HO—A$^1$—(OH)$_u$                                                              (IV)

wherein
    A$^1$ is a straight chain or branched chain aliphatic radical with 2 to 36 carbon atoms or a cycloaliphatic radical both of which are unsubstituted or substituted by substituents which do not themselves react under the conditions of the process and
    u is an integer which is smaller by at least the number 1 than the number of carbon atoms of the radical A$^1$ which can be substituted.

3. Process of claim 2 wherein u is an integer from 1 to 5.

4. Process of claim 2 wherein A$^1$ is an aliphatic radical of 2 to 20 carbon atoms or a cycloaliphatic radical of 5 to 18 carbon atoms.

5. Process of claim 1 wherein the hydroxy compound used in step (a) has the formula

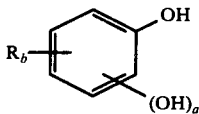
(II)

wherein
R is independently from each other hydrogen, halogen, alkyl or phenyl or two radicals R which are substituents on adjacent carbon atoms can form, conjointly with these carbon atoms, a carbocyclic or heterocyclic 5-membered or 6-membered ring,
$a$ is 1, 2 or 3 and
$b$ is $5 - a$.

6. Process of claim 1 wherein the hydroxy compound used in step (a) has the formula

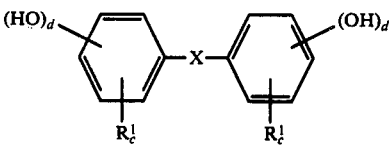
(III)

wherein
X is oxygen, $SO_2$, CO, a $CH_2$ chain with up to 6 carbon atoms, which is optionally substituted by $C_1$-$C_4$ alkyl or by phenyl, a cycloaliphatic or aromatic 5-membered or 6-membered ring or a single bond, and
$R^1$ is independently from each other hydrogen, halogen, alkyl or phenyl or two radicals $R^1$ which are substituents on adjacent carbon atoms can form, conjointly with these carbon atoms, a carbocyclic or heterocyclic 5-membered or 6-membered ring, or
$R^1$ is a group having the formula

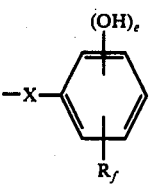

wherein
X is as defined above,
R is independently from each other hydrogen, halogen, alkyl or phenyl or two radicals R, which are substituents on adjacent carbon atoms, can form, conjointly with these carbon atoms, a carbocyclic or heterocyclic 5-membered or 6-membered ring,
$e$ is 1, 2 or 3,
$f$ is $5 - e$ and
$c$ is $5 - d$ and
$d$ is 1, 2 or 3.

7. Process of claim 1 wherein the compound used in step (a) has the formula (V)

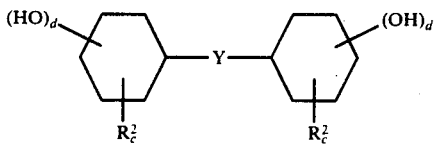
-continued wherein
C is oxygen, $SO_2$, CO, a $CH_2$ chain with up to 6 carbon atoms, which is optionally substituted by $C_1$-$C_4$ alkyl or by phenyl, a cycloaliphatic or aromatic 5-membered or 6-membered ring or a single bond, and
$R^2$ is independently from each other hydrogen, halogen, alkyl or phenyl or two radicals $R^2$, which are substituents on adjacent carbon atoms, can form, conjointly with these carbon atoms, a carbocyclic or heterocyclic 5-membered or 6-membered ring, or
$R^2$ is a group having the formula

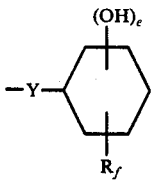

wherein
Y is as defined above,
R is independently hydrogen, halogen, alkyl or phenyl or two radicals R, which are substituents or adjacent carbon atoms, can form, conjointly with these carbon atoms, a carbocyclic or heterocyclic 5-membered or 6-membered ring,
$e$ is 1, 2 or 3,
$f$ is $5 - e$
$c$ i $5 - d$ and
$d$ is 1, 2 or 3.

8. Process of claim 1 wherein the hydroxy compound is a polyester, polyether or polyurethane with at least two free hydroxyl groups.

9. Process of claim 8 wherein the polyester, polyether or polyurethane has two or three free hydroxy groups.

10. Process of claim 1 wherein the hydroxy compound is condensed in step (a) with cyanuric chloride in solution in the presence of about 1 mol of base per mol of hydrogen chloride to be split off.

11. Process of claim 1 wherein the condensation product obtained in step (a) is condensed with the aromatic hydroxy compound in solution in the presence of about 1 mol of base per mol of hydrogen chloride to be split off.

12. Process of claim 10 wherein the base used in step (a) and/or step (b) is an alkali metal hydroxide, alcoholate or carbonate, or a tertiary amine.

13. Process of claim 10 wherein the condensation reaction in step (a) and/of step (b) is effected at from 0° to 150° C.

14. Process of claim 1 wherein the condensation reactions in steps (a) and (b) are effected in the melt at a temperature of from 100° to 220° C.

15. Process of claim 14 wherein the condensation reactions are effected at a pressure of between 0.2 and 0.8 bar.

16. Process of claim 1 wherein the free hydroxyl groups of the condensation product obtained in step (b) are reacted with a cyanogen halide in step (c) in the presence of a solvent and at a temperature of between 0° and 65° C.

17. Process of claim 1 wherein the base used in step (c) is an alkali meal hydroxide, alcoholate or carbonate or a tertiary amine.

18. Process of claim 1 wherein the cyanogen halide is cyanogen bromide or cyanogen chloride.

19. Process of claim 1 wherein a molar ratio of phenolic hydroxyl groups to cyanogen halide to base of 1:1:1 is employed in step (c).

20. Process of claim 1 wherein the hydroxy compound is condensed in step (a) with cyanuric chloride in suspension in the presence of about 1 mol of base per mol of hydrogen to be split off.

21. Process of claim 1 wherein the condensation product obtained in step (a) is condensed with the aromatic hydroxy compound in suspension in the presence of about 1 mol of base per mol of hydrogen chloride to be split off.

* * * * *

UNITED STATES PATENT AND TRADEMARK OFFICE
CERTIFICATE OF CORRECTION

PATENT NO. : 4,049,630
DATED : September 20, 1977
INVENTOR(S) : Rudolf Sundermann et al It is certified that error appears in the above-identified patent and that said Letters Patent are hereby corrected as shown below:

Column 1, line 35, "chloride" should read -- chlorine --.

Column 2, line 10, "haloen" should read -- halogen --.

Column 3, line 4, "isopropy" should read -- isopropyl --.

Column 3, line 39, delete "4" fourth occurrence.

Column 3, line 51, "4,4 ∝" should read ' -- 4,4'- --.

Column 4, line 53, "2,4 pentanediol" should read -- 2,4-pentanediol --.

Column 5, line 63, "Hochtlen" should read -- Höchtlen --.

Column 8, line 1, insert -- same -- before "solvents" second occurrence.

Column 13, line 52, "95%" should read -- 94% --.

Column 14, line 33, "where" should read -- which --.

UNITED STATES PATENT AND TRADEMARK OFFICE
CERTIFICATE OF CORRECTION

PATENT NO. : 4,049,630
DATED : September 20, 1977
INVENTOR(S) : Rudolf Sundermann et al It is certified that error appears in the above-identified patent and that said Letters Patent are hereby corrected as shown below:

Column 14, line 41, "the" should read -- then --.

Column 18, line 49, delete " ' " after "-40".

Column 20, line 10, "C" should read -- Y --.

Column 20, line 33, insert -- from each other -- after "independently".

Signed and Sealed this

Fourth Day of April 1978

[SEAL]

Attest:

RUTH C. MASON
Attesting Officer

LUTRELLE F. PARKER
Acting Commissioner of Patents and Trademarks